United States Patent
Lewis et al.

(10) Patent No.: US 7,665,212 B2
(45) Date of Patent: Feb. 23, 2010

(54) METHODS FOR MANUFACTURING ENDODONTIC INSTRUMENTS

(75) Inventors: Paul Lewis, Midvale, UT (US); John Nielsen, Cottonwood Heights, UT (US)

(73) Assignee: Ultradent Products, Inc., South Jordan, UT (US)

(*) Notice: Subject to any disclaimer, the term of this patent is extended or adjusted under 35 U.S.C. 154(b) by 605 days.

(21) Appl. No.: 11/063,354

(22) Filed: Feb. 23, 2005

(65) Prior Publication Data

US 2006/0185169 A1     Aug. 24, 2006

(51) Int. Cl.
*A61C 5/10*     (2006.01)
(52) U.S. Cl. .................. 29/896.1; 409/73; 409/192; 433/165; 433/197; 433/198; 433/224
(58) Field of Classification Search ............. 29/896.1; 433/197, 198, 102, 224, 165; 409/131–132, 409/192, 203, 213, 217, 73, 75–76; 72/205
See application file for complete search history.

(56) References Cited

U.S. PATENT DOCUMENTS

| | | | |
|---|---|---|---|
| 1,372,170 A | 3/1921 | Judd | |
| 2,173,218 A | 9/1939 | Zoppi | |
| 2,390,254 A | 12/1945 | Henkle | |
| 2,434,286 A | 1/1948 | Pfann | |
| 2,640,253 A | 6/1953 | Fink et al. | |
| 2,701,505 A | 2/1955 | Fink | |
| 2,712,775 A | 7/1955 | Wilt | |
| 2,724,918 A * | 11/1955 | Triman | 156/345.15 |
| 2,907,151 A | 10/1959 | Peterson | 51/281 |
| 3,055,241 A * | 9/1962 | Hedgecock et al. | 72/205 |
| 3,406,555 A | 10/1968 | Fuchs et al. | |
| 3,803,014 A | 4/1974 | Atkinson | |
| 3,823,514 A | 7/1974 | Tsuchiya | |
| 3,869,373 A | 3/1975 | Schacher et al. | |

(Continued)

FOREIGN PATENT DOCUMENTS

EP     0119714     9/1984

(Continued)

OTHER PUBLICATIONS

Office Action dated May 6, 2005 cited in related U.S. Appl. No. 10/436,938.

(Continued)

*Primary Examiner*—Rick K Chang
(74) *Attorney, Agent, or Firm*—Workman Nydegger

(57) ABSTRACT

Endodontic instruments having a desired cutting edge are formed, at least in part, using a cold forming process. The method of forming the endodontic instrument includes providing a blank metal thread or wire and at least one die that has a negative impression of a cutting edge. The die is pressed against the blank with sufficient force in order for the die to form an at least partially formed cutting edge in the blank. Any desired shape can be formed into the blank by selecting a die with the proper corresponding negative impression. Cold forming techniques suitable for forming endodontic instruments include roll forming, flat rolling, radial forming, cold drawing, and similar techniques. The files can be sharpened or otherwise modified before or after cold-forming using techniques such as cutting, grinding, and chemical milling.

37 Claims, 6 Drawing Sheets

U.S. PATENT DOCUMENTS

| | | | |
|---|---|---|---|
| 3,894,570 A * | 7/1975 | Reynolds | 411/333 |
| 3,905,156 A | 9/1975 | Vogelsanger | 51/46 |
| 3,911,713 A | 10/1975 | Vydrin et al. | 72/205 |
| 3,948,073 A | 4/1976 | Lovell | |
| 4,116,755 A | 9/1978 | Coggins et al. | |
| 4,604,884 A | 8/1986 | Matsutani | |
| 4,611,509 A | 9/1986 | Matsutani | 76/24 R |
| 4,934,934 A | 6/1990 | Arpaio, Jr. et al. | 433/102 |
| 5,028,228 A | 7/1991 | Ubukata et al. | 425/298 |
| 5,219,284 A * | 6/1993 | Velvart et al. | 433/102 |
| 5,382,319 A | 1/1995 | Tumminaro, Jr. | |
| 5,477,604 A | 12/1995 | Smith et al. | 29/558 |
| 5,527,332 A | 6/1996 | Clement | |
| 5,539,973 A | 7/1996 | Smith et al. | 29/558 |
| 5,616,255 A | 4/1997 | Tumminaro, Jr. | |
| 5,620,537 A | 4/1997 | Bampton | |
| 5,628,674 A | 5/1997 | Heath et al. | 451/48 |
| 5,637,089 A | 6/1997 | Abrams et al. | |
| 5,644,834 A | 7/1997 | Smith et al. | 29/557 |
| 5,653,590 A | 8/1997 | Heath et al. | 433/102 |
| 5,682,665 A | 11/1997 | Svanberg | |
| 5,714,115 A | 2/1998 | Speidel et al. | |
| 5,741,429 A | 4/1998 | Donadio, III et al. | |
| 5,762,497 A | 6/1998 | Heath | |
| 5,762,541 A | 6/1998 | Heath et al. | 451/48 |
| 5,762,811 A | 6/1998 | Munoz | |
| 5,782,145 A | 7/1998 | Metzger | |
| 5,807,106 A | 9/1998 | Heath | |
| 5,882,198 A | 3/1999 | Taylor et al. | |
| 5,928,144 A | 7/1999 | Real | |
| 5,941,760 A | 8/1999 | Heath et al. | |
| 5,984,679 A | 11/1999 | Farzin-Nia et al. | |
| 6,018,860 A | 2/2000 | Smith et al. | 29/558 |
| RE36,628 E | 3/2000 | Sagae et al. | |
| 6,086,773 A | 7/2000 | Dufresne et al. | |
| 6,126,521 A | 10/2000 | Shearer et al. | 451/48 |
| 6,149,742 A | 11/2000 | Carpenter et al. | |
| 6,213,771 B1 | 4/2001 | Fischer | |
| 6,258,182 B1 | 7/2001 | Schetky et al. | |
| 6,287,210 B1 | 9/2001 | Janusz et al. | |
| 6,299,445 B1 | 10/2001 | Garman | |
| 6,315,558 B1 | 11/2001 | Farzin-Nia et al. | |
| 6,375,458 B1 | 4/2002 | Moorleghem et al. | |
| 6,399,215 B1 | 6/2002 | Zhu et al. | |
| 6,428,634 B1 | 8/2002 | Besselink et al. | 148/421 |
| 6,575,747 B1 | 6/2003 | Riitano et al. | |
| 6,581,430 B2 | 6/2003 | Wilson | |
| 6,702,579 B1 * | 3/2004 | Hoppe et al. | 433/102 |
| 6,729,026 B2 | 5/2004 | Garcia et al. | 29/882 |
| 6,793,838 B2 * | 9/2004 | Hansen et al. | 216/100 |
| 6,865,919 B2 | 3/2005 | Litwinski et al. | |
| 6,890,134 B1 | 5/2005 | Wagner et al. | |
| 7,077,755 B2 | 7/2006 | Keener et al. | |
| 7,083,687 B2 | 8/2006 | Tanaka et al. | |
| 7,094,055 B2 * | 8/2006 | Senia et al. | 433/102 |
| 7,207,111 B2 | 4/2007 | Aloise et al. | |
| 7,223,100 B2 * | 5/2007 | Brock et al. | 433/102 |
| 2002/0137008 A1 | 9/2002 | McSpadden et al. | 433/102 |
| 2002/0182565 A1 | 12/2002 | Senia et al. | 433/102 |
| 2003/0068597 A1 | 4/2003 | Garman | 433/102 |
| 2004/0099356 A1 | 5/2004 | Wu | |
| 2004/0121283 A1 | 6/2004 | Mason | 433/102 |
| 2004/0126734 A1 | 7/2004 | Senia et al. | 433/102 |
| 2004/0229188 A1 | 11/2004 | Lewis et al. | 433/102 |
| 2004/0241037 A1 | 12/2004 | Wu | |
| 2005/0069837 A1 | 3/2005 | Lewis et al. | 433/102 |
| 2005/0109158 A1 | 5/2005 | Keener | |
| 2006/0014480 A1 | 1/2006 | Aloise et al. | |
| 2006/0027046 A1 | 2/2006 | Kugelberg et al. | |
| 2006/0086440 A1 | 4/2006 | Boylan et al. | |
| 2006/0185169 A1 | 8/2006 | Lewis et al. | |
| 2006/0185170 A1 | 8/2006 | Lewis et al. | |

FOREIGN PATENT DOCUMENTS

| | | |
|---|---|---|
| JP | 2002144154 | 5/2002 |

OTHER PUBLICATIONS

Notice of Allowance dated Jul. 14, 2005 cited in related U.S. Appl. No. 10/436,938.

Office Action dated Oct. 22, 2007 cited in related U.S. Appl. No. 10/991,178.

Notice of Allowance dated Apr. 3, 2008 cited in related U.S. Appl. No. 10/991,178.

Notice of Allowance dated Sep. 20, 2007 cited in related U.S. Appl. No. 11/282,852.

Office Action dated Oct. 2, 2008 from U.S. Appl. No. 11/063,757.

* cited by examiner

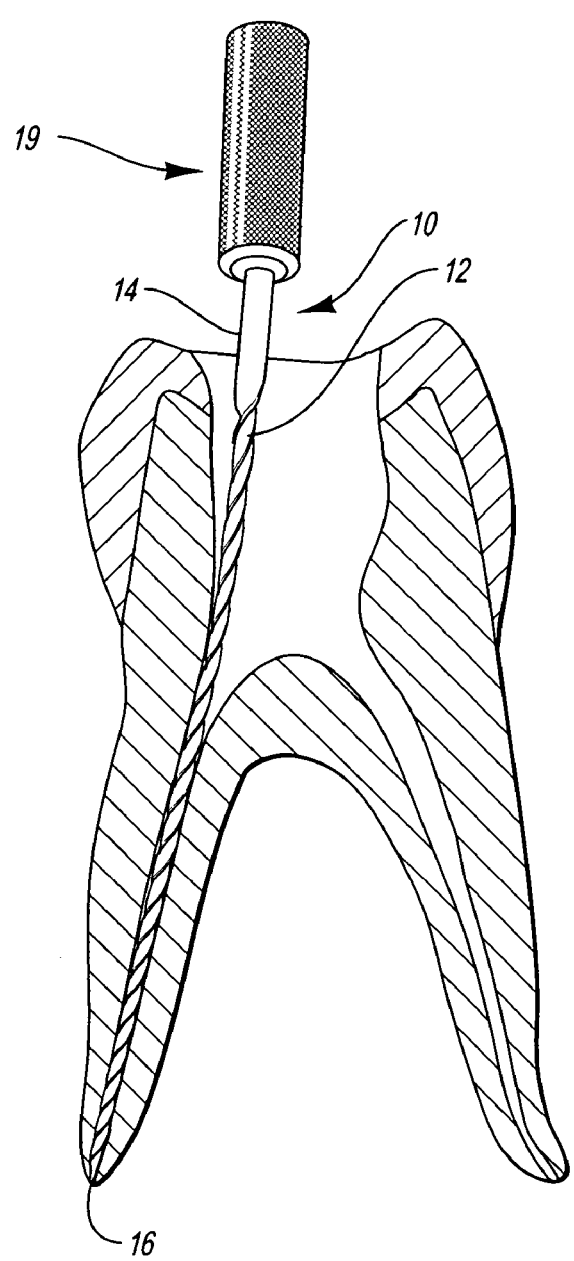
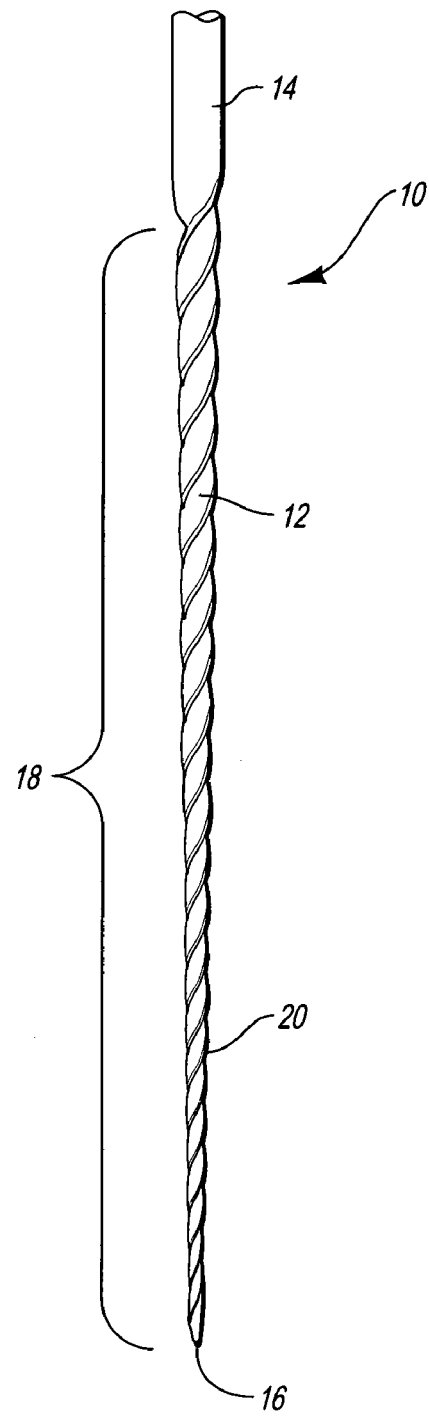
FIG. 1
FIG. 2

METHODS FOR MANUFACTURING ENDODONTIC INSTRUMENTS

BACKGROUND OF THE INVENTION

1. The Field of the Invention

The present invention relates to the manufacture of endodontic instruments. More particularly, the invention relates to a cold forming process for manufacturing endodontic files.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material forming the nerve of the tooth that has become infected and, after careful preparation of the canal that contained the nerve material, refill the canal with an inert filling material, such as gutta percha, permitting a patient to retain the tooth.

To achieve a successful root canal restoration, the dental practitioner must carefully and, as completely as possible, remove the infected pulp material of the tooth to prevent continued or future infection of surrounding tissues. The removal process typically includes shaping the root canal so that it can be effectively and successfully filled and sealed with an inert material. Filling and sealing minimizes the possibility of further infection occurring within the cleaned and shaped root canal.

Cleaning and shaping the root canal in preparation of sealing and filling the root canal is achieved by the use of metal files. The metal files have cutting surfaces for removing tissue in the root canal. The cutting surfaces are typically formed by helical flutes formed in the file. One or more helical cutting surfaces may be provided, which may be axially spaced as desired.

Some existing endodontic instruments and manufacturing methods are described in U.S. Pat. Nos. 4,934,934, 5,653,590, and 5,762,541.

Since root canals are seldom straight, often having bends and twists, at least some endodontic files are advantageously flexible. Currently preferred materials of construction include stainless steel, and more recently, nickel-titanium (Ni—Ti) alloys. Such materials, especially Ni—Ti alloys, exhibit good flexibility, resilience and strength, and are not likely to fail during use. Flexibility and strength are important to avoid file breakage during the cleaning process.

Current methods of manufacturing metal endodontic files require time intensive and costly methods. For example, stainless steel endodontic files are typically machined to form a cutting edge and then twisted to make a flute along the file's axis.

Another existing method of manufacturing existing endodontic files uses a grinding technique to form a cutting edge. In the grinding operation, a metallic (typically a titanium alloy) rod is advanced past a rotating grinding wheel at a relatively slow feed rate. The depth of cut may be varied along the length of the rod to produce a tapered endodontic file having a helical flute. Such a method is disclosed in U.S. Pat. No. 5,762,541.

While current manufacturing methods are capable of producing endodontic files in a variety of different shapes and sizes using a variety of different metals, there is still a great need to reduce the costs of manufacturing endodontic files. Forming an endodontic file from raw materials is currently a significant expense in the endodontic manufacturing process. One problem with current processes is the time it takes to form each piece. For example, forming a cutting edge by grinding a metal wire can take more than a minute for each piece and the grinding machine can cost hundreds of thousand of dollars.

Another problem with endodontic manufacturing processes is they fail to reduce or sometimes cause stress fractures or weaknesses in the metal of the file. Even minor imperfections in the metal of an endodontic file can be problematic. Endodontic files are very thin, thus small imperfections can cause the file to break during use. A broken file in a root canal is very difficult to remove and can cause damage to the root canal.

Therefore, what is needed is a manufacturing process that can reduce the cost of manufacturing endodontic files while maintaining or improving the strength of the endodontic file.

BRIEF SUMMARY OF THE INVENTION

The present invention provides improved methods for manufacturing endodontic instruments such as endodontic files. The methods of the present invention use one or more types of cold forming techniques to form a cutting edge or a partially formed cutting edge in a piece of deformable material.

In an exemplary embodiment, the invention involves the steps of (a) providing a blank comprising a deformable material; (b) providing at least one die comprising a negative impression that corresponds to at least a partially formed cutting edge of an endodontic instrument; and (c) cold forming the blank using the at least one die and sufficient force to form at least a partially formed cutting edge in the blank.

Cold forming can be performed using any suitable technique. Examples of suitable techniques include cold rolling, flat rolling, radial forming, and cold drawing.

The cold forming die can be used to form any number of cutting edges and to form a cutting edge with any desired shape. In one embodiment, cold forming the blank with one or more dies produces a blank having a polygonal cross section. The apexes of the polygonal cross section yield at least partially formed cutting edges.

The shape of the negative impression can determine how sharp the cutting edge is following the cold forming process. In one embodiment, the cutting edge is formed to shape during cold forming such that the cutting edge is ready for use without further processing. In an alternative embodiment, the cutting edge is partially formed and further processing is needed before the final cutting edge is formed. For example, the cutting edge may need to be sharpened using a process such as chemical milling. Whether sharpening is required can depend on the precision of the cold forming process, the size of the cutting edge on the instrument and the sharpness required for a particular use of the instrument.

Additional manufacturing steps that can be included in various embodiments of the present invention include cutting, grinding, machining, chemical milling, electrochemical milling, laser micromachining, grit blasting and combinations of these. These additional processing techniques can be used in various embodiments of the invention to further sharpen the partially formed cutting edge, dull the tip of the endodontic instrument, and/or provide a taper along the endodontic instrument.

The present invention provides many advantages for manufacturing endodontic instruments over the methods of the prior art. Because the cutting edge is at least partially formed by the cold-forming process, the cutting edge is very inexpensive to form. The cold forming process of the present invention can form the cutting edge in seconds. Many existing systems require minutes to form the cutting edge. Further-more, the machinery used to perform cold forming is relatively inexpensive as compared to the cost of machinery for existing methods of manufacturing endodontic instruments.

Another significant advantage of using a cold forming step in the manufacture of endodontic instruments is the improvement in the properties of the material. The methods of the present invention are able to produce an endodontic instrument that is superior to existing endodontic instruments because the cold forming step hardens the material and/or removes imperfections such as micro cracks and fissures. The improved endodontic instruments of the present invention are less likely to fatigue and break off inside a root canal because of these improved material properties. Because working within the root canal of a person can be very difficult, avoiding broken endodontic instruments by using endodontic instruments manufactured according to the disclosed methods can be very beneficial for dental practitioners and their clients.

These and other benefits, advantages and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1 is a cross sectional view of a tooth with an endodontic instrument positioned in one of two root canals;

FIG. 2 is a perspective view of the cutting portion of an exemplary endodontic instrument;

DETAILED DESCRIPTION OF EXEMPLARY EMBODIMENTS

Figure 3A:
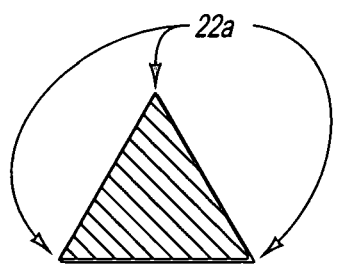
FIGS. 3A-3G illustrate different polygonal transverse cross sections of the cutting portion of several exemplary endodontic instruments manufactured according to the method of the present invention.

A detailed description of the endodontic instruments and manufacturing methods of the present invention will now be provided, with specific reference to figures illustrating preferred embodiments of the invention. It will be appreciated that like structures will be provided with like reference designations. To provide context for interpreting the scope of the invention, certain terms used throughout the application will now be defined.

As used herein, the terms endodontic "instrument" and endodontic "instruments" refer to endodontic files and other instruments used in a root canal or other endodontic procedure.

As used herein, the terms "polygon" and "polygonal" refer to a shape that is closed and bounded by straight or curved sides. Non-limiting examples include a triangle, a square, a rectangle, a pentagon, a spherical triangle, or any other of various regular or irregular shapes.

As used herein, the terms "chemical milling," "stripping" and "etching" refer to a procedure whereby a material is worked or shaped by exposure to a chemical bath. While exposed to the chemical bath, the shaping occurs as layers of metal are "stripped" or "etched" off because of the chemical action of the bath.

I. Exemplary Endodontic Instruments

Referring to FIGS. 1 and 2, an exemplary endodontic instrument 10 is illustrated which comprises a metallic rod 12 having a proximal end 14, and a distal end 16. At least a portion of the metallic rod 12 comprises a cutting portion 18, which is disposed between the proximal end 14 and the distal end 16. In this embodiment, the cutting portion 18 includes at least one helical cutting edge 20 that extends helically around metallic rod 12. A handle 19 is provided adjacent proximal end 14 of metallic rod 12 to facilitate gripping of the endodontic instrument 10 by a user or to provide attachment to dental tool (e.g., a rotating or reciprocating hand piece).

The cutting portion 18 is preferably tapered between the proximal end 14 and the distal end 16, with decreasing diameter or width toward the distal end 16. The taper can be continuous or incremental (i.e., stair-stepped). The taper can be any amount desired, but is preferably between about 0.02 mm/mm and about 0.06 mm/mm. The specific taper of any instrument depends on the intended use and dental practitioner preference. For example, a taper of 0.0225 mm/mm may be preferred when preparing a root canal that is to receive a gutta percha cone having a taper of about 0.02 mm/mm.

The cutting portion 18 may have a length of about 2 mm up to the full length of the rod 12, which may be as much as about 30 mm or more. In the illustrated embodiment, the cutting portion 18 has a length sufficient to extend substantially the full depth of a tooth root canal as illustrated in FIG. 1. It will be appreciated, however, that the cutting portion may terminate before reaching the distal end 16, as in a coronal file, or comprise a small length near distal end 16, as in an apical file. Terminating or reducing the length of the cutting portion 18 near distal end 16 creates a blunt tip that helps prevent undesirable penetration or ledging of the instrument 10 into the root of the tooth or through the apex of the root.

The cutting portion 18 of the instrument illustrated in FIGS. 1 and 2 has a cross-sectional configuration that is triangular and is composed of three linear sides, as best seen in FIG. 3A. The apices 22a of the triangle form cutting edges 20. In other embodiments, the cutting portion 18 may be of any polygonal cross-section such that when the rod is torsioned, helical cutting edges are formed.

Figure 3B:
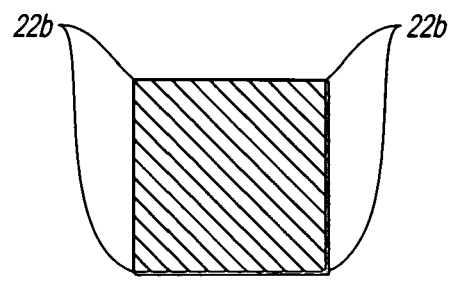
Figure 3C:
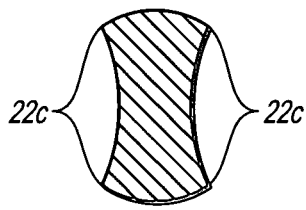

Several non-limiting examples of suitable polygonal cross-sections are illustrated in FIGS. 3A-3G. FIG. 3A illustrates a triangular cross section in which apices 22a form three cutting edges 20. FIG. 3B illustrates a square cross section in which line intersections 22b form four cutting edges. FIG. 3C illustrates a cross section bounded by four curved sides, two of which are concave and two of which are convex. The intersections 22c between the convex and concave sides form four cutting edges.

Figure 3D:
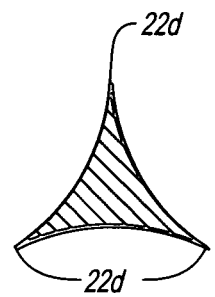
Figure 3E:
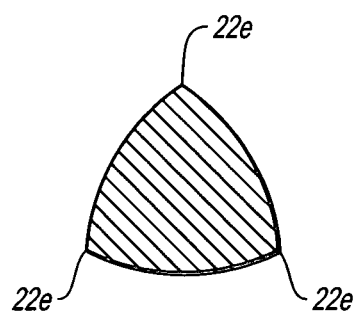

FIGS. 3D and 3E illustrate alternative spherical triangular cross sections, with the triangle cross section of FIG. 3D having concave surfaces between the apices 22d of the triangle and with the triangle cross section of FIG. 3E having convex surfaces between apices 22e of the triangle.

Figure 3F:
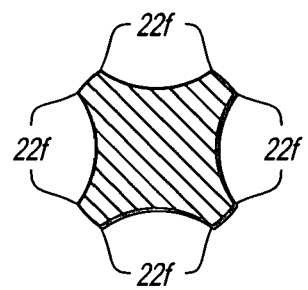
Figure 3G:
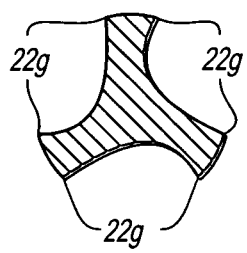

FIG. 3F illustrates a cross section bounded by a combination of four concavely curved sides separated by four straight sides. The intersection 22f between the straight and curved sides form eight cutting edges. FIG. 3G illustrates a cross section of an irregular polygon bounded by three concavely curved sides separated by three convexly curved sides. The intersections 22g between the six curved sides yield six cutting surfaces.

In an exemplary embodiment, the apices or edges 22a-22g of the various cross sections form helical cutting edges. In one embodiment, the helix is formed simultaneously with the formation of the cutting edge or the partially formed cutting edge. In an alternative embodiment twisting of the intermediate is used to form helical edges.

As described below, the endodontic instruments of the present invention are at least partially formed by performing a cold forming step. In an exemplary embodiment, during the cold forming step, the endodontic instrument is cold worked. This cold working improves the material properties of the endodontic file by removing some or all of the micro cracks and fissures (i.e., by reducing the number of dislocations in the crystal lattice of the metal in the blank). Since all larger cracks begin with micro cracks or fissures, the endodontic instruments of the present invention are less susceptible to cracking and breaking.

II. Method of Manufacture

Exemplary methods of manufacturing endodontic instruments according to the present invention include forming at least a partially formed cutting edge in a piece of material using a cold forming technique. The steps of an exemplary embodiment include (a) providing a blank comprising a deformable material; (b) providing at least one die comprising a negative impression that corresponds to at least a partially formed cutting edge of an endodontic instrument; and (c) cold forming the blank using the at least one die and sufficient force to form at least a partially formed cutting edge in the blank.

In addition to forming at least a partially formed cutting edge, the methods of the present invention also include making various modifications to the cold-formed endodontic instrument. Exemplary modifications include forming a taper, making the tip of the endodontic instrument more blunt, and/or shaping the cutting edge to form a helix, such as by twisting the endodontic instrument.

A. Providing a Blank

In an exemplary embodiment, the blank used in the methods of the present invention is a metallic thread or wire. The metallic thread or wire can be selected to have a diameter that is close to the desired final diameter of the endodontic instrument.

With regard to wire thickness, endodontic instruments are sized in accordance with established standards, which range from a thickness at the distal end 16 of 1.4 mm (size 140) to a thickness at the distal end 16 of 0.06 mm (size 06). Selecting a diameter that is close to, or identical to the diameter of the final product, reduces the amount of flow that the material will have to undergo in the cold forming process and/or reduces the amount of material that will have to be removed in a subsequent modification step.

A manufacturer typically has the ability to modify the blank before and after cold forming. Thus, a blank can have any desired feature such as a taper or a partially formed cutting edge prior to cold forming. In other words, the blank need only be "blank" as to the feature that is formed during the cold forming process.

The blank used in the methods of the present invention can be made from any material that is sufficiently deformable that it can be cold formed. Preferred materials for forming the endodontic instruments of the present invention include stainless steels and titanium based alloys, such as nickel titanium. Stainless steel alloys are preferred for their relative inexpensive cost, good performance, and biological inertness. Titanium based alloys are typically preferred for their strength and flexibility.

Examples of suitable titanium based alloys include nickel titanium, nickel-titanium-chromium alloy, a nickel-titanium-copper alloy, a nickel-titanium-niobium alloy, or any other super-elastic metallic material. Although any suitable material can be used to make the endodontic instruments of the present invention, titanium-based alloys are preferred because they are strong yet flexible and resilient. In one preferred embodiment, a nickel titanium alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients which do not adversely affect the suitability of the material for use as an endodontic instrument.

Another exemplary titanium-based alloy includes metal atoms selected from group IV and V transition metals and oxygen. Examples of such alloys include alloys having formulas of 1Ti-12Ta-9Nb-3V-6Zr-1O and 1Ti-23Nb-0.7Ta-2Zr-1O (mole percent). Additional details regarding these alloys are described in co-pending U.S. Provisional Application No. 60/586,738, entitled "Dental Abrading Instruments Made From Super-Elastic Alloys," and filed Jul. 9, 2004, which is incorporated herein by reference.

Other materials suitable for cold forming can be used in the methods of the present invention. Those skilled in the art of cold forming are familiar with the different types of materials and techniques that can be used in a cold forming process. Those skilled in the art are readily accustomed to determining whether a particular metal will work in a particular system.

B. Providing at Least One Die

The methods of the present invention utilize one or more dies to stamp, mold, or otherwise form a desired shape into the blank. The dies have a negative impression that corresponds to a finished cutting edge or partially formed cutting edge of an endodontic instrument. The cutting edges illustrated in FIGS. 3A-3G, and discussed above, are examples of features to which the negative impression of the die can correspond. The negative impression can also correspond to other features of an endodontic instrument such as a taper or a blunt tip.

The negative impression can be completely formed in a single die or alternatively, the negative image can be spread across more than one die such that the use of the plurality of dies creates the proper corresponding cutting edge. The negative impression is also formed by accounting for the movement of the dies relative to the blank during the cold forming process. One advantage of using multiple dies is that the forces generated in the cold forming process can be spread across more than one die, thus reducing localized forces.

The negative impression can be formed into the die by grinding or etching the die or using other known techniques. Those skilled in the art of cold forming are familiar with forming negative impressions that correspond to desired features to be formed in a cold forming process.

C. Cold Forming

The method of the present invention includes using at least one cold forming technique to form a finished cutting edge or a partially formed cutting edge. Various cold forming techniques can be used to form a cutting edge in the blank. Suitable cold forming techniques include roll forming, radial forming, flat rolling, cold drawing, and similar techniques.

Figure 4A:
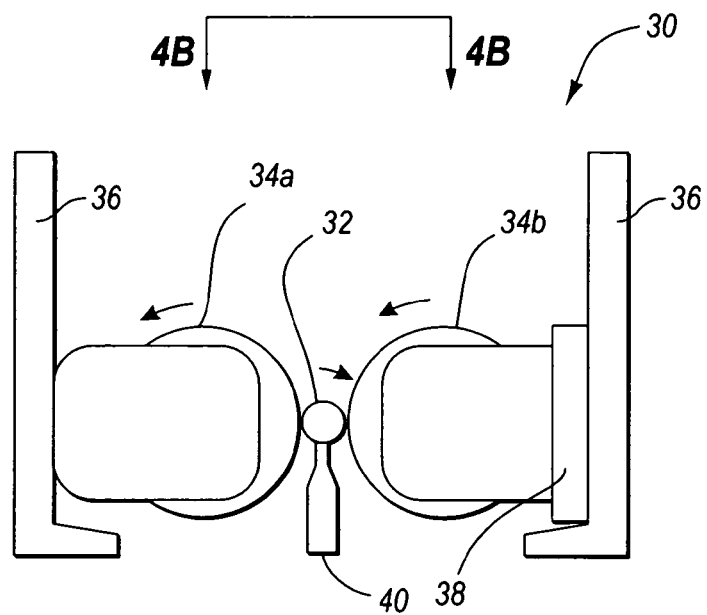
FIG. 4A is a schematic illustrating formation of a cutting edge of an endodontic instrument using a roll forming apparatus according to an exemplary embodiment of the present invention.

FIG. 4 schematically illustrates an exemplary apparatus 30 for roll forming a cutting edge in a blank 32. Roll forming apparatus 30 includes roll dies 34a and 34b. Roll dies 34a and 34b have a negative image of one or more desired features to be pressed into blank 32. Roll dies 34a and 34b are attached to a frame 36 and rotate about a horizontal axis. Roll die 34b can move relative to roll die 34a through the actuation of hydraulic press 38. A holder 40 positions the blank 32 between roll dies 34a and 34b. During the roll forming process, hydraulic press 38 forces roll dies 34a and 34b toward each other until the dies engage blank 32. Roll dies 34a and 34b are caused to rotate in the same direction, which causes blank 32 to rotate in an opposite direction. As roll dies 34a and 34b rotate, the negative image on dies 34a and 34b is pressed into blank 32.

Figure 4B:
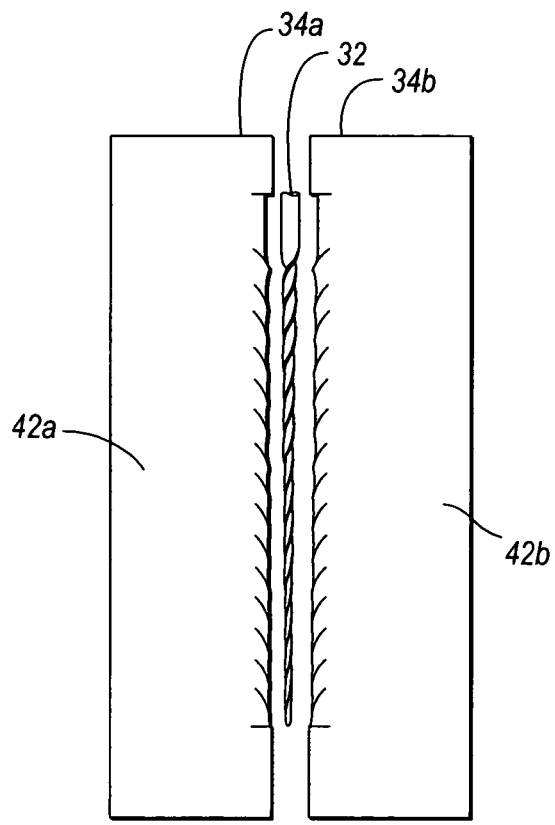
FIG. 4B is a top exploded view of the rollers and blank of FIG. 4A, where roll forming has been performed to form a cutting edge on the blank.

FIG. 4B shows an exploded perspective view of dies 34a and 34b engaging blank 32a. The surfaces 42a and 42b or dies 34a and 34b respectively show the negative impression of dies 34a and 34b. The negative impression corresponds to an at least partially formed cutting edge and a taper of an endodontic instrument. The rotation of dies 34a and 34b have formed an at least partially formed cutting edge and a taper in blank 32a.

In an exemplary embodiment, blank 32a is a piece of metallic wire or thread. Various techniques can be used to feed blank 32a into roll dies 34a and 34b. For example, blank 32a can be a wire that is continuously fed into rollers 34a and 34b by the threading force of the rollers. Alternatively, blank 32a can be rolled and removed. In addition, blank 32a can be cut to the correct length before, during, or after cold forming.

Figure 5:
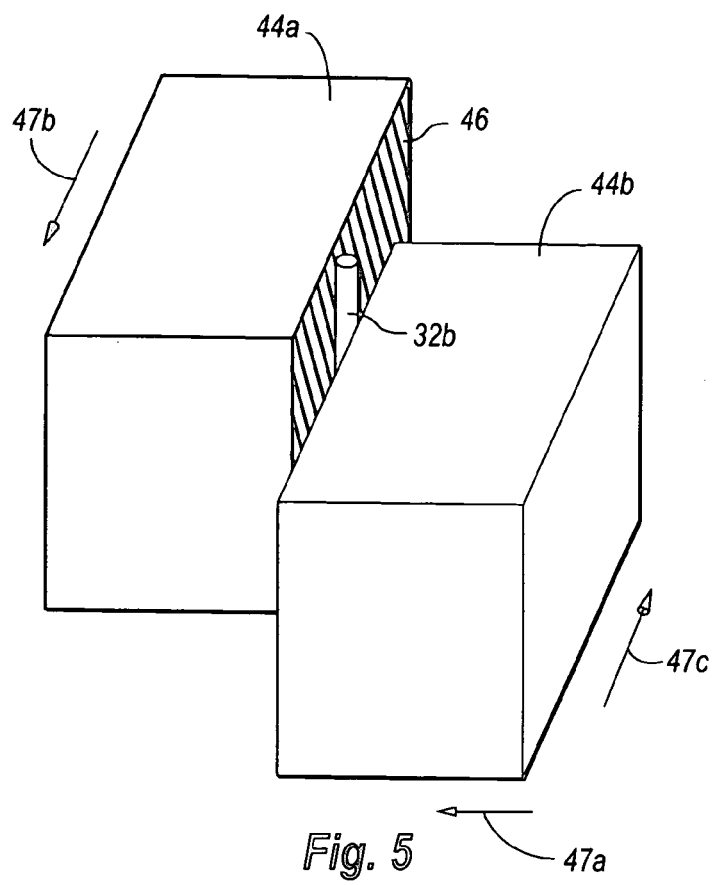
FIG. 5 is a schematic illustrating formation of a cutting edge of an endodontic instrument using a flat rolling apparatus according to an exemplary embodiment of the present invention.

In another embodiment of the invention, a blank is cold formed by flat rolling. FIG. 5 shows dies 44a and 44b that can be used in a flat rolling apparatus to form an endodontic instrument according to the present invention. In this embodiment, surface 46 of die 44a has a negative impression that corresponds to an at least partially formed cutting edge. The opposing surface of die 44b likewise has a negative impression that corresponds to an at least partially formed cutting edge.

Dies 44a and 44b are used to form an at least partially formed cutting edge in blank 32b by using a flat rolling apparatus, which presses dies 44a and 44b together to engage blank 32b as indicated by arrow 47a. Dies 42a and 42b are also caused to slide relative to one another as indicated by arrows 47b and 47c. As dies 44a and 44b slide relative to one another, blank 32b is rolled and the negative impression on the surfaces of dies 44a and 44b form an at least partially formed cutting edge. In another embodiment, dies 44a and 44b are configured to form a taper in the blank in addition to forming the cutting edge.

Figure 6:
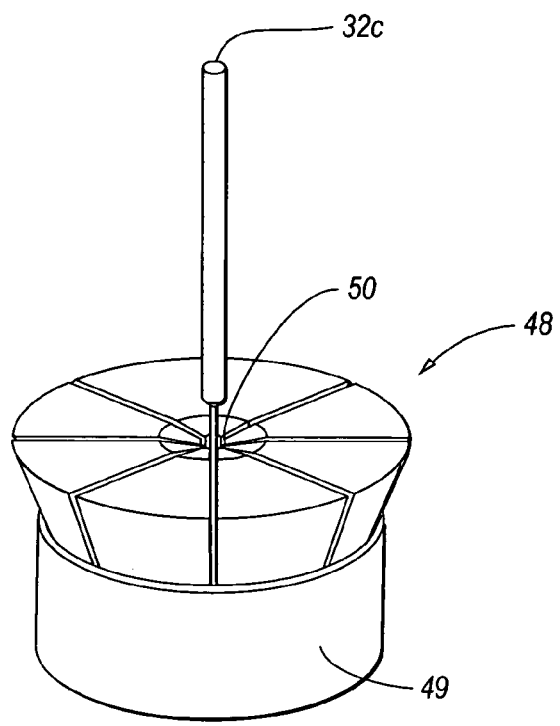
FIG. 6 is a schematic illustrating formation of a cutting edge of an endodontic instrument using a radial forming apparatus according to an exemplary embodiment of the present invention.

In yet another embodiment of the present invention, a radial forming process is used to form an endodontic instrument. FIG. 6 shows a set of radial dies 48 within an actuating ring 49. The set of radial dies 48 and actuating ring 49 are used in a radial forming apparatus generally known to those skilled in the art. The dies 48 have a negative impression on the surfaces that form cavity 50. The negative impression corresponds to an at least partially formed cutting edge and/or a taper of an endodontic instrument. These features are formed into blank 32c, positioned within dies 48, by forcing actuating ring 49 up around dies 48. As actuating ring 49 moves up, dies 48 are forced radially toward blank 32c. Dies 48 engage blank 32c and the negative impression on dies 46 forms an at least partially formed cutting edge and/or taper in blank 32c.

Figure 7A:
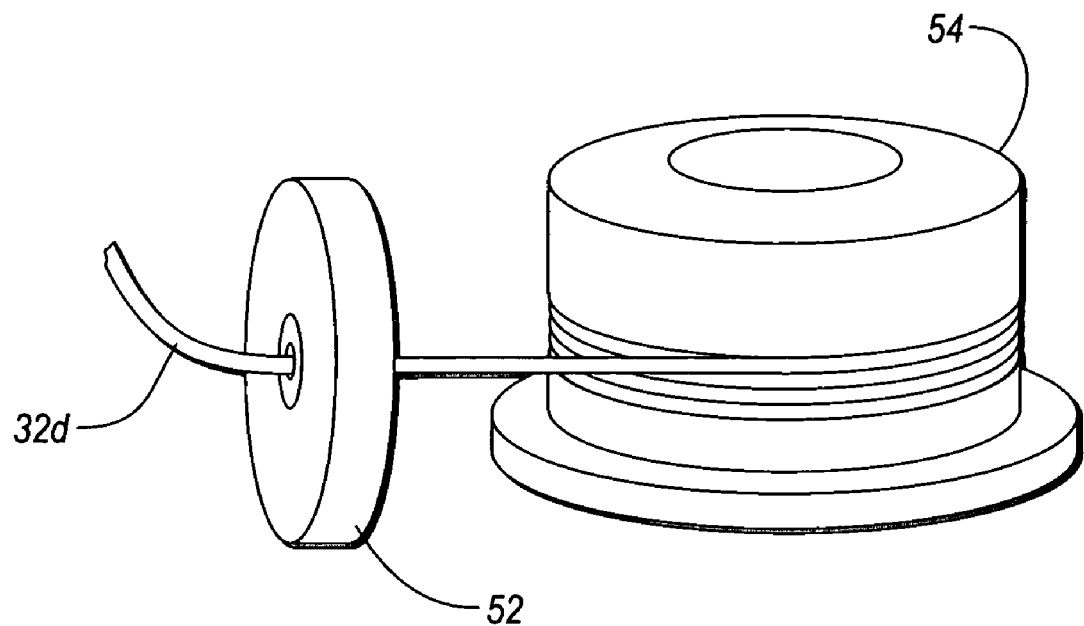
FIG. 7A is a schematic illustrating formation of a partially formed cutting edge of an endodontic instrument using a wire drawing technique according to an exemplary embodiment of the present invention.
Figure 7B:
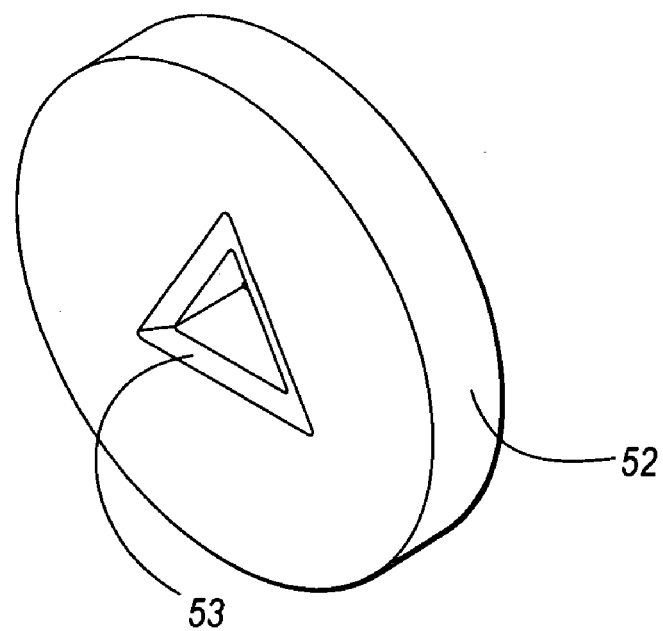
FIG. 7B is a perspective view of a die used in the wire drawing technique illustrated in FIG. 7A.

In another embodiment, a cold drawing process is used to form a cutting edge or a partially formed cutting edge in a blank. FIG. 7A shows a blank 32d in the form of an uncut metallic wire that is drawn through die 52 and spooled on draw block 54. As shown in FIG. 7B, die 52 has a negative impression 53 that corresponds to a triangular shape. As blank 32d is drawn through die 52, blank 32d is formed into a triangular shape. Blank 32d can be cut to a proper length before or after being drawn through die 52. Blank 32d can also be only partially drawn through die 52 such that a portion of blank 32d is not triangular. Leaving a portion of blank 32d unshaped can be advantageous for adding a handle to the endodontic instrument. In addition, as discussed more fully below, a cold drawn piece having a polygonal cross section can be twisted to create a helical cutting edge.

In some embodiments of the present invention, two or more cold forming steps are performed to provide the desired feature or features. In an exemplary embodiment, in a first cold forming step a taper or partially formed taper is formed into a blank. In a subsequent step, a cutting edge or a partially formed cutting edge is formed into the blank. However, in an alternative embodiment, the taper and cutting edge can be formed in a single cold forming process. Those skilled in the art will be able (based on the present disclosure) to recognize the number and types of cold forming techniques that can be performed on a particular material.

Additional cold forming techniques can be used to form an at least partially formed cutting edge and/or other feature of an endodontic instrument according to the present invention. For example, other forms of rolling using non-symmetrical wheels or more than two wheels can be used. In addition, techniques such as extrusion and swagging can be used to form a cutting edge or a partially formed cutting edge.

The methods of forming an endodontic instrument using cold forming according to the present invention make it possible to form an endodontic instrument with almost any desired cross section. The endodontic instruments can have any desired taper and can have non-uniform features. Thus using the cold forming techniques of the present invention, the shape of the endodontic instrument can be selected to provide beneficial properties such as flexibility, in addition to desired cutting properties.

In some embodiments of the present invention, cold forming does not produce a finished product. For example, in some embodiments, cold forming does not produce a cutting edge that is sufficiently sharp or tapered. Whether a dental instrument is sufficiently sharp can depend on the preferences of the dental practitioner or the application that the instrument will be used in. Thus, in some embodiments of the present invention, additional steps or modifications, which are discussed below, may be needed. In these cases, the cold forming process produces an intermediate instrument. Nevertheless, even where cold forming only produces an intermediate instrument, the cold forming step or steps of the present invention can have many cost saving advantages by eliminating costly manufacturing processes, reducing the use of a costly manufacturing process, or by providing the opportunity to use an entirely new and cheaper process.

D. Additional Modifications to Intermediate Instruments

Additional steps can be performed to further modify the cold-formed blank to provide additional or enhanced features. For example, manufacturing the endodontic instruments can include forming a taper, sharpening the cutting edge, dulling the tip, forming a helical cutting edge, providing a grip or similar features.

Figure 8:
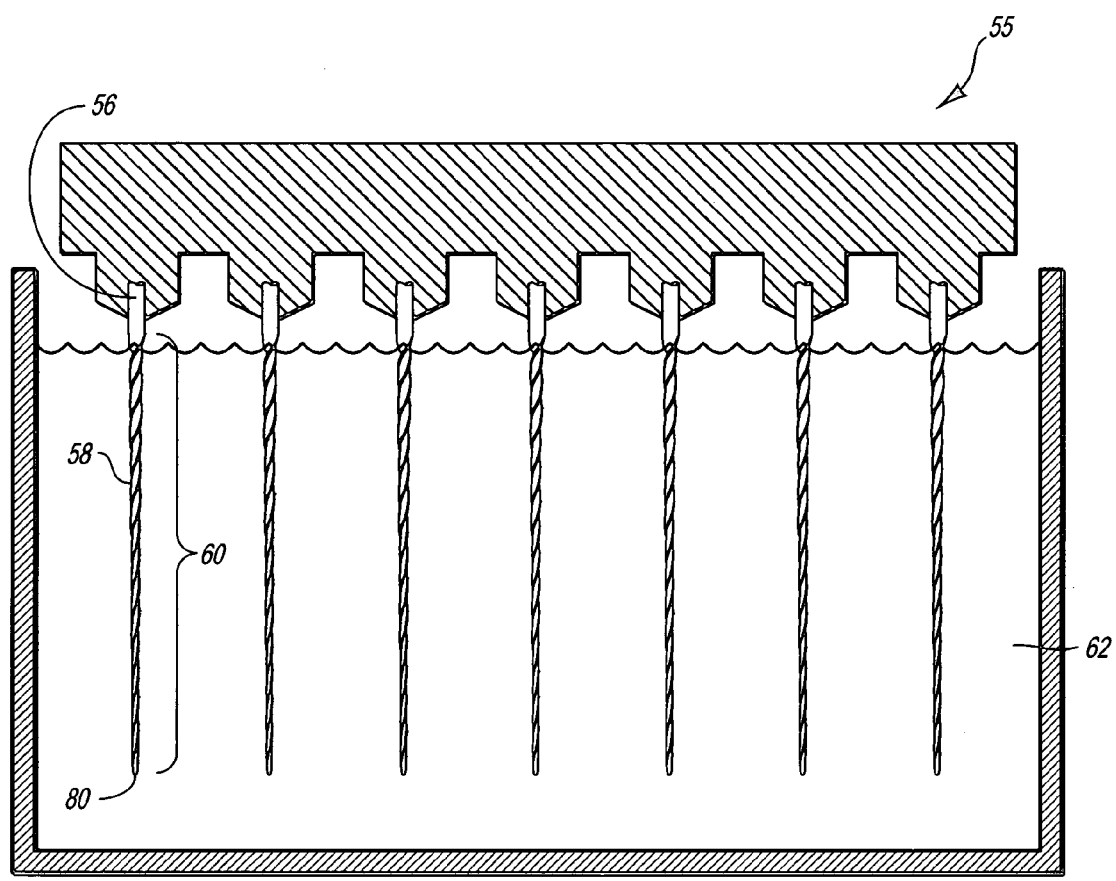
FIG. 8 is a schematic illustrating chemical milling of a plurality of endodontic instruments to sharpen the cutting edge of each of the plurality of endodontic instruments.

Various processes can be used to sharpen the cutting edge and/or form a taper In an exemplary embodiment, a chemical milling process is used to sharpen the partially formed cutting edge, thereby producing a finished cutting edge. FIG. 8 shows an exemplary apparatus 55 for chemically milling an intermediate endodontic instrument 56 having a taper and partially formed cutting edge 58 along cutting portion 60. Any number of intermediate instruments can be simultaneously chemically milled as illustrated by the additional intermediate endodontic instruments illustrated in FIG. 8.

To chemically mill cutting edge 58 along portion 60, the intermediate endodontic instruments are submerged in chemical milling composition 62. In an exemplary embodiment, chemical milling composition includes an acid, water, and a wetting agent. Suitable acids include hydrofluoric acid and nitric acid. One currently preferred composition includes about 10% hydrofluoric acid, about 20% nitric acid, about 0.8% Dapco 6001, a wetting agent, and the balance water (% by volume).

In another embodiment, electrodes are connected to the chemical milling apparatus and the endodontic instruments such that a current passes through the chemical milling composition and the endodontic instrument. The current passing through the composition can heat the composition to increase the rate of the chemical milling reaction and/or to remove material from the surface of the intermediate endodontic file by electrolysis. For purposes of this invention, the use of chemical milling and electrolysis is referred to as electrochemical milling.

Chemically milling a partially formed cutting, edge sharpens the edge because the chemical milling process removes an even layer of material from the surface. As material is evenly removed, the width of the cutting edge become progressively thinner, thus sharpening the cutting edge.

In an another embodiment, intermediate instruments can also be tapered using a chemical milling process. The cutting portion 60 of each intermediate instrument is tapered by progressively inserting or withdrawing cutting portion 60 from chemical milling composition 62. The portions of the endodontic instrument that remain in chemical milling composition 62 for a longer period have more material removed. By withdrawing the endodontic instrument out of the chemical milling composition at a slow continuous rate, an even taper is formed.

In the case of instruments that are further processed by grinding or machining, chemical milling can be used to remove micro fissures or cracks caused by grinding that can easily propagate during use, causing fracture of the file in a person's root canal. Chemical milling can remove such cracks, yielding a superior contiguous surface and a file that is more resistant to breakage during use.

Additional aspects of chemical milling endodontic instruments is described in co-pending U.S. application Ser. No. 10/436,938, entitled "Methods of Manufacturing Endodontic Instruments," filed May 13, 2003, and co-pending U.S. application Ser. No. 10/991,178, entitled "Methods for Manufacturing Endodontic Instruments," filed Nov. 17, 2004, both of which are incorporated herein by reference.

Methods of manufacturing the endodontic instruments of the present invention can include the use of other known techniques such as cutting, grinding, machining, laser micro-machining, grit blasting and combinations of these. A more detailed description of an exemplary machining or grinding process is set forth in U.S. Pat. No. 5,762,541, which is incorporated by reference with respect to machining or include the cold forming processes as disclosed herein. These techniques can be used to sharpen the cutting edge, create a taper, or otherwise modify the endodontic instrument. For example, some endodontic instruments are formed to have a somewhat dulled or blunt tip such that the tip of the endodontic instrument does not pierce through the walls of the root canal or cause ledging. Dulling the tip can be economically accomplished using a grinder.

In some exemplary embodiments, cold forming produces an intermediate instrument that requires torsioning or twisting to form a helical cutting edge. Torsioning is typically accomplished by holding one end of the cutting portion stationary while twisting the opposite end. Torsioning an intermediate instrument can cause the apices of polygonally-shaped instrument to be twisted to form helical cutting surfaces along the cutting portion. Endodontic instruments typically have a helical cutting edge. Helical cutting edges are advantageous because they can cut or remove tissue as a practitioner turns the instrument in the root canal or moves the instrument up and down within the root canal.

The endodontic instruments and methods of manufacturing endodontic instruments, according to the present invention, provide many advantages over the instruments and methods of the prior art. Forming the cutting edge or partially forming the cutting edge using the cold-forming processes described herein greatly reduces the time and expense for manufacturing endodontic instruments. In addition, cold-forming the endodontic instruments improves the material properties of the instruments thereby reducing the likelihood of breakage during an endodontic procedure.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing an endodontic instrument, comprising:
   (a) providing a blank comprising a deformable material;
   (b) providing at least one die comprising a negative impression that corresponds to an essentially finished endodontic instrument having at least three essentially finished and continuous cutting edges spaced around a longitudinal axis of the endodontic instrument and that has a length and width so as to be readily insertable within a root canal of a tooth; and
   (c) cold working the blank using the at least one die comprising the negative impression to form an essentially finished endodontic instrument having at least three essentially finished and continuous cutting edges spaced around a longitudinal axis of the endodontic instrument and that has a length and width so as to be readily insertable within a root canal of a tooth.

2. A method as recited in claim 1, wherein cold working is performed by at least one of roll forming, radial forming, flat rolling, or cold drawing.

3. A method as recited in claim 2, wherein the blank is cold worked by roll forming it using the die with the negative impression corresponding to a polygonal cross section, and wherein the roll forming of the blank using the die with the negative impression yields an endodontic instrument having a polygonal cross-section.

4. A method as recited in claim 3, further comprising torsioning the endodontic instrument to yield at least three continuous helical cutting edges.

5. A method as recited in claim 4, wherein the at least three continuous helical cutting edges are subsequently sharpened by chemical milling.

6. A method as recited in claim 3, wherein the polygonal cross section is at least one of a square, a triangle, a polygon having straight surfaces, a polygon having concave surfaces, or a polygon having convex surfaces.

7. A method as recited in claim 6, wherein the endodontic instrument is further modified by torsioning the instrument to form helical cutting edges.

8. A method as recited in claim 3, further comprising further modifying the endodontic instrument by chemically milling at least a portion of the cutting edges.

9. A method as recited in claim 8, wherein chemically milling is performed by progressively inserting and/or withdrawing the endodontic instrument from a chemical milling composition at a predetermined rate in order to taper the instrument.

10. The method as recited in claim 8, wherein the cutting edges are is chemically milled using a solution of hydrofluoric acid and/or nitric acid, water, and a wetting agent in order to sharpen the cutting edges.

11. A method as recited in claim 1, wherein the blank comprises a metallic thread or wire.

12. A method as recited in claim 1, wherein the deformable material comprises stainless steel or a titanium-based alloy.

13. A method as recited in claim 1, further comprising further modifying the endodontic instrument by further sharpening at least one of the essentially finished and continuous cutting edges subsequent to cold working the blank.

14. A method as recited in claim 13, wherein further sharpening the at least three essentially finished and continuous cutting edges is performed by one or more of cutting, grinding, machining, chemically milling, electrochemical milling, laser micromachining, or grit blasting.

15. A method as recited in claim 1, wherein providing a blank comprises providing a tapered metallic thread or wire having a diameter that decreases from a proximal end to a distal end and that is formed by at least one of cold forming, cutting, grinding, machining, chemically milling, electrochemical milling, laser micromachining, or grit blasting.

16. A method as recited in claim 1, further comprising tapering the endodontic instrument by chemical milling.

17. A method as recited in claim 1, wherein the negative impression of the die further corresponds to a tapered endodontic file having a diameter that decreases from a proximal end to a distal end so that cold working the blank yields a tapered endodontic instrument having a diameter that decreases from a proximal end to a distal end.

18. A method as recited in claim 1, wherein the negative impression further corresponds to a blunt tip of an endodontic instrument so that cold working the blank yields an endodontic instrument having a blunt tip.

19. A method as recited in claim 1, further comprising further modifying the endodontic instrument by dulling a tip of the endodontic instrument by at least one of cutting, grinding, machining, chemical milling, electrochemical milling, laser micromachining, grit blasting or combinations thereof.

20. A method of manufacturing an endodontic instrument, comprising:
   (a) providing a blank comprising a deformable material;
   (b) providing at least one die comprising a negative impression that corresponds to an essentially finished endodontic instrument having at least three essentially finished and continuous cutting edges spaced around a longitudinal axis of the endodontic instrument and that has a length and width so as to be readily insertable within a root canal of a tooth; and
   (c) rolling the blank using the at least one die comprising the negative impression and with sufficient force to form an endodontic instrument having an at least three essentially finished and continuous cutting edges spaced around a longitudinal axis of the endodontic instrument and that has a length and width so as to be readily insertable within a root canal of a tooth.

21. A method as recited in claim 20, wherein rolling the blank comprises one of roll forming, flat rolling, or a combination thereof.

22. A method as recited in claim 20, wherein rolling the blank yields an endodontic instrument having a polygonal cross-section.

23. A method as recited in claim 22, wherein the polygonal cross section is at least one of a square, a triangle, a polygon having straight surfaces, a polygon having concave surfaces, or a polygon having convex surfaces.

24. A method as recited in claim 20, further comprising chemically milling the endodontic instrument in order to sharpen at least a portion of the at least three cutting edges.

25. The method as recited in claim 24, wherein the cutting edges are chemically milled using a solution of hydrofluoric acid and/or nitric acid, water, and a wetting agent.

26. A method of manufacturing an endodontic instrument, comprising:
   (a) providing a blank comprising a deformable material;
   (b) providing a die comprising a negative impression that corresponds to an essentially finished endodontic instrument having a polygonal cross section, at least three partially finished and continuous cutting edges spaced around a longitudinal axis of the endodontic instrument, and a length and width so as to be readily insertable within a root canal of a tooth;
   (c) rolling the blank using the at least one die comprising the negative impression and with sufficient force to form an endodontic instrument having a polygonal cross-section, at least three partially finished and continuous cutting edges spaced around a longitudinal axis of the endodontic instrument, and a length and width so as to be readily insertable within a root canal of a tooth; and
   (d) torsioning the endodontic instrument in order to transform the at least three partially finished and continuous cutting edges into helical cutting edges.

27. A method as recited in claim 26, wherein rolling comprises roll forming or flat rolling.

28. The method as recited in claim 26, wherein the polygonal cross-section formed in (c) using the die comprising the negative impression is at least one of a square, a triangle, a polygon having straight surfaces, a polygon having concave surfaces, or a polygon having convex surfaces.

29. A method as recited in claim 26, further comprising sharpening the at least three partially finished and continuous cutting edges and/or helical cutting edges by chemical milling.

30. A method as recited in claim 26, wherein the die comprising the negative impression corresponds to an endodontic instrument having a taper from a promixal end to a distal end and rolling the blank forms an endodontic instrument having a taper from the promixal end to the distal end.

31. A method of manufacturing an endodontic instrument, comprising:
   (a) providing an untapered blank comprising a deformable material;
   (b) providing at least one die comprising a negative impression that corresponds to a tapered endodontic instrument having a diameter that decreases from a proximal end to a distal end of the endodontic instrument and a length and width so as to be readily insertable within a root canal of a tooth; and
   (c) rolling the blank using the at least one die and sufficient force to form a tapered endodontic instrument having a diameter that decreases from the proximal end to the distal end of the endodontic instrument and a length and width so as to be readily insertable within a root canal of a tooth.

32. A method as recited in claim 31, wherein the negative impression of the die also corresponds to an at least partially formed cutting edge of an endodontic instrument so that rolling the blank further comprises forming an at least partially formed cutting edge in the endodontic instrument.

33. A method as recited in claim 32, wherein the at least partially formed cutting edge is helical.

34. A method as recited in claim 31, further comprising:
   providing at least one other die comprising a negative impression that corresponds to an at least partially formed cutting edge of an endodontic instrument; and
   rolling the endodontic instrument formed in (c) using the at least one other die and sufficient force to form an at least partially formed cutting edge in the endodontic instrument.

35. A method as recited in claim 34, wherein the at least partially formed cutting edge is helical.

36. A method of manufacturing an endodontic instrument, comprising:
   (a) providing a blank comprising a deformable material;
   (b) providing at least one die comprising a negative impression that corresponds to three or more at least partially formed cutting edges spaced around a longitudinal axis of an essentially finished endodontic instrument having a taper and a length and width so as to be readily insertable within a root canal of a tooth; and
   (c) cold working the blank using the at least one die comprising the negative impression and with sufficient force to form an essentially finished endodontic instrument having three or more at least partially formed cutting edges spaced around a longitudinal axis of the essentially finished endodontic instrument having a taper and a length and width so as to be readily insertable within a root canal of a tooth.

37. A method of manufacturing an endodontic instrument, comprising:
   (a) providing a blank comprising a deformable material;
   (b) providing at least one die comprising a negative impression that corresponds to three or more at least partially formed cutting edges spaced around a longitudinal axis of an endodontic instrument having a length and width so as to be readily insertable within a root canal of a tooth;
   (c) rolling the blank using the at least one die and sufficient force to form an endodontic instrument having three or more at least partially formed cutting edges spaced around a longitudinal axis of the endodontic instrument and a length and width so as to be readily insertable within a root canal of a tooth; and
   (d) sharpening the at least partially formed cutting edges by chemical milling.

\* \* \* \* \*